United States Patent [19]
Levy

[11] Patent Number: 5,236,360
[45] Date of Patent: Aug. 17, 1993

[54] OPTICAL MEMBERS FOR LASER TRANSMISSION

[75] Inventor: Guy Levy, Tustin, Calif.

[73] Assignee: Laser Medical Technology, Inc., San Clemente, Calif.

[21] Appl. No.: 917,285

[22] Filed: Jul. 23, 1992

[51] Int. Cl.$^5$ ............................................. A61C 5/00
[52] U.S. Cl. ..................................... 433/215; 606/16; 606/2; 385/142
[58] Field of Search ............... 385/142, 141, 143, 144, 385/147; 372/117, 41; 128/303.1, 397, 398; 606/17, 3, 2, 14, 15, 16; 433/215

[56] References Cited

U.S. PATENT DOCUMENTS

| | | | |
|---|---|---|---|
| 4,428,646 | 1/1984 | Lighty | 385/142 X |
| 4,658,817 | 4/1987 | Hardy | 128/303.1 X |
| 4,676,242 | 6/1987 | Doi | 128/303.1 X |
| 5,074,861 | 12/1991 | Schneider et al. | 606/17 |

Primary Examiner—John D. Lee
Assistant Examiner—Phan T. Heartney
Attorney, Agent, or Firm—Spensley Horn Jubas & Lubitz

[57] ABSTRACT

An optical member for transmission of laser radiation, the fiber comprising a light transmitting element containing calcium fluoride.

14 Claims, 1 Drawing Sheet

OPTICAL MEMBERS FOR LASER TRANSMISSION

BACKGROUND OF THE INVENTION

The present invention relates to optical fibers for delivering laser radiation, particularly for medical and dental treatments.

It is known that optical fibers provide an effective means for applying laser radiation to regions to be treated in connection with medical and dental procedures. These procedures include cutting of both hard and soft tissues, cauterization and sterilization, among others. Investigations of the effects of laser radiation have resulted in the development of procedures which permit increased energy levels of such radiation to be utilized safely and effectively for a variety of purposes. It should be expected that further studies will lead to further increases in the energy levels which can produce useful results.

However, one impediment to such progress is the energy levels which can be transmitted by optical fibers without subjecting them to damage or destruction. While it is known that the level of radiation energy which can be conducted by a fiber is proportional to the fiber diameter, so that increases in the energy level being conducted can be achieved by increasing fiber diameter, larger fiber diameters are disadvantageous for many procedures of the type here under consideration. By way of example, fibers which are to be employed in connection with dental treatments, and particularly endodontic treatments, must have very small diameters. This is also the case when fibers are to be used to conduct laser radiation along blood vessels or other body passages. In addition, the flexibility of such fibers decreases as their diameter increases.

Accordingly, continuing efforts have been made to provide optical fiber compositions capable of conducting high laser energy levels without damage.

SUMMARY OF THE INVENTION

It is a primary object of the invention to provide optical fiber compositions having this characteristic.

Another object of the invention is to provide novel optical fibers which can be employed in virtually any medical or dental apparatus for the purpose of conducting laser radiation to body regions to be treated.

Yet another object of the invention is to provide optical fibers which can be employed with virtually any type of laser source.

The above and other objects are achieved, according to the invention, by an optical fiber for transmission of laser radiation, the fiber comprising a light transmitting element containing calcium fluoride.

In effect, it has been found that calcium fluoride is highly transparent to certain laser radiation wavelengths and can transmit high energy levels without experiencing damage.

Moreover, calcium fluoride has a lower melting point than silica and is biologically compatible to a high degree. Therefore, when laser radiation is delivered from a fiber composed of or containing calcium fluoride, to a tooth or bone tissue, the heat generated by interaction of the radiation with that tissue can act to melt the distal end, or tip, of the fiber and the melted fiber material can flow into a tooth canal or an opening in the tooth or bone material to provide a dense, voidfree, biologically compatible filling or coating.

DESCRIPTION OF THE PREFERRED EMBODIMENTS

Figure 1:
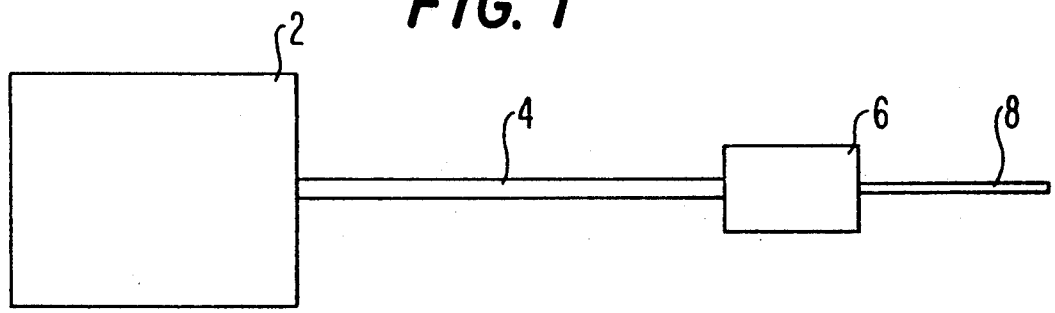
FIG. 1 is a pictorial view of a medical or dental device employing an optical fiber according to the present invention.

FIG. 1 illustrates, in simplified pictorial form, a medical or dental apparatus which may employ optical fibers according to the invention. The apparatus includes a laser unit 2, which may be any of the types of lasers currently being used or investigated for medical or dental purposes, having an output connected to an optical transmission fiber 4. Fiber 4 has an output end mounted in a handpiece 6 and an output fiber 8 is optically coupled, within handpiece 6, to fiber 4. Fiber 8 may be used directly to apply laser radiation to a body region to be treated, or may be introduced, for example via a catheter, into a body passage, such as a blood vessel, in order to carry out various types of treatment. Alternatively, radiation may be emitted directly from handpiece 6, in which case fiber 8 would be eliminated.

According to a primary feature of the invention, fiber 4 and/or 8 consists of or contains crystalline calcium fluoride, which has been found to have the capability of conducting extremely high laser radiation power levels without experiencing damage or destruction. Investigations performed thus far suggest that this advantage is attained at least for the Nd:YAG wavelength of 1.06 $\mu$, and it is believed that a similar result will be achieved for other laser radiation wavelengths which are capable of being transmitted via conventional silica fibers.

Figure 2:
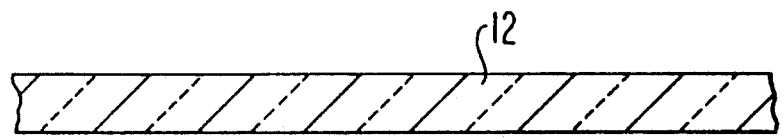
FIG. 2 is a cross-sectional view of one embodiment of a fiber according to the invention.

An optical fiber according to the invention may be a simple fiber 12 having a homogenous cross section, as shown in FIG. 2, in which case the composition may consist entirely of calcium fluoride, with trace amounts of impurities, or may be composed predominantly of calcium fluoride, or may contain calcium fluoride as a minor ingredient. While it presently appears that the improved high energy transmission capability of fibers according to the invention is dependent on their content of calcium fluoride, improvements over the prior art may be realized even with fibers having less than 50% calcium fluoride content.

Figure 3:
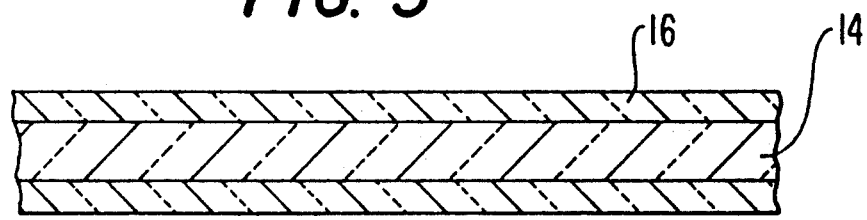
FIG. 3 is a cross-sectional view of a second embodiment of a fiber according to the invention.

The embodiment shown in FIG. 3 is constituted by a core 14 enclosed by a cladding 16. In this embodiment, one or both of the core and cladding may have a composition as described above with respect to FIG. 2.

According to preferred embodiments of the invention, the homogenous fiber of FIG. 2, or core 14 and cladding 16 of FIG. 3, will each have the maximum calcium fluoride content compatible with other optical and physical properties, including refractive index, flexibility and stress resistance.

Figure 4:
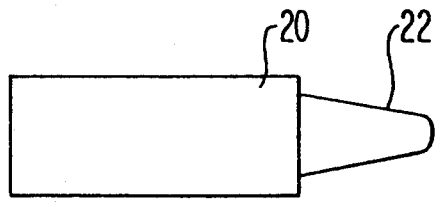
FIG. 4 is a pictorial view of a further medical device provided with an embodiment of the invention.

A composition according to the invention may additionally be utilized as a contact tip for a handpiece used for laser surgery. FIG. 4 illustrates such a device, which includes a handpiece 20 carrying a contact tip 22. Contact tip 22, which may be disposable, has a composition as described above, including a content of calcium fluoride sufficient to enable the tip to conduct high laser radiation energy levels without experiencing damage or destruction. Such a tip constitutes a less expensive alternative to the sapphire tips currently employed in such devices.

When fiber 4 of FIG. 1 has the form shown in FIG. 2, it may be made of calcium fluoride alone or a mixture of calcium fluoride and other radiation transparent materials, such as silica. When fiber 4 of FIG. 1 has the form shown in FIG. 3, core 14 may be made entirely or principally of calcium fluoride and cladding 16 may be made of silica or other materials having good mechanical strength.

Optical fiber 8 of FIG. 1 may have a tapered distal end, particularly when it is to be used for widening a root canal. When fiber 8 has the form shown in FIG. 2, it may be made entirely of calcium fluoride or a mixture of calcium fluoride and other materials such as silica. When the fiber is to be used to fill a root canal or to fill or coat an opening in a tooth or bone, at least its distal end is preferably made entirely of calcium fluoride. When fiber 8 has the form shown in FIG. 3, at least cladding 16 is made entirely of calcium fluoride. Core 14 may also be made of calcium fluoride, or of a mixture of calcium fluoride and other materials, such as silica, having good mechanical strength, or entirely of such other materials.

As regards the contact tip 22 shown in FIG. 4, it may be tapered, as shown, or not tapered, and can be made entirely of calcium fluoride or may consist of a core of other materials, such as silica, with a calcium fluoride coating. In either case, the heat generated when laser radiation emitted from the tip interacts with tooth or bone tissue may melt the calcium fluoride so that it will fill or coat openings in the tissue.

To prepare crystalline calcium fluoride, a solution containing calcium ions is reacted with a solution containing fluoride ions. For example, adding a calcium nitrate solution to a soluble ammonium fluoride solution will result in the production of calcium fluoride, precipitated as solid calcium fluoride, and NH$_4$NO$_3$.

The precipitated solid calcium fluoride is in the form of a very fine powder. To produce larger granules or a solid body of calcium fluoride, ceramic techniques can be employed. For example, a mass of the fine calcium fluoride powder can be compressed to form a green cake. The green cake can then be sintered to form a shaped piece of calcium fluoride. The melting point of the calcium fluoride remains near 1400° C.

After a shaped piece of calcium fluoride has been produced in the manner described above, it may be heated to a temperature close to its melting point in order to soften the calcium fluoride, without causing it to melt. While in the softened state, the shaped piece is stretched to assume approximately the shape of an optical fiber. The shaped piece may be extruded around a silica core to form a fiber as shown in FIG. 3. Then, after having cooled, the piece is ground and polished to the desired final dimensions.

After completion of the above-described manufacturing process, the resulting calcium fluoride fiber may be coated, or clad, with hard plastic, silica, or other appropriate material. Such cladding, as shown in FIG. 3, maintains the structural integrity of a calcium fluoride fiber to enable the fiber to be bent to at least a certain extent while avoiding breakage or damage to the calcium fluoride core. A fiber consisting essentially only of calcium fluoride tends to experience breakage when subjected to bending. Cladding, as shown in FIG. 3 of hard plastic, silica, or similar material will tend to maintain the structural integrity of the calcium fluoride core.

According to other embodiments of the invention, the calcium fluoride powder may be mixed with other ingredients prior to sintering. These other ingredients would be constituted by materials selected to have the requisite transparency to the radiation to be transmitted and to be capable of undergoing the sintering and subsequent stretching operations without experiencing damage or destruction.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A device for delivering laser radiation to an opening in tooth or bone tissue, said device comprising a laser and an optical member comprising a light transmitting element having a distal end containing calcium fluoride connected for conducting radiation from said laser to the opening, wherein said laser is operable to supply radiation to the distal end of said light transmitting element at an intensity sufficient to cause heat generated by interaction of the radiation with the tooth or bone tissue to melt the distal end of said light transmitting element to cause material of said light transmitting element, including calcium fluoride, to flow into the opening in the tooth or bone tissue to provide a dense, void-free, biologically compatible filling or coating.

2. The device as claimed in claim 1 wherein said optical member is in the form of an optical fiber comprising a core and a cladding layer surrounding said core.

3. The device as defined in claim 2 wherein said core constitutes said element.

4. The device as defined in claim 2 wherein both said core and said cladding contain fluoride.

5. The device as claimed in claim 2 wherein said core contains at least 50% calcium fluoride, by weight.

6. The device as defined in claim 2 wherein said cladding contains at least 50% calcium fluoride, by weight.

7. The device as claimed in claim 2 wherein said core consists substantially entirely of calcium fluoride.

8. The device as defined in claim 2 wherein said cladding consists substantially entirely of calcium fluoride.

9. The device as claimed in claim 1 wherein the distal end of said element consists substantially entirely of calcium fluoride.

10. The device as defined in claim 1 wherein the distal end of said element contains at least 50% calcium fluoride, by weight.

11. The device as defined in claim 1 wherein said optical member is an optical fiber.

12. The device as claimed in claim 1 wherein said light transmitting element is an optical fiber dimensioned for introduction into the opening.

13. The device as defined in claim 1 wherein said light transmitting element constitutes a contact tip for emitting radiation to the opening.

14. A method for filling or coating an opening in tooth or bone tissue using the device defined in claim 1, comprising: positioning the distal end of the light transmitting element at the opening; and operating the laser to deliver radiation via the light transmitting element to the tissue in the opening at an intensity sufficient to cause heat to be generated by interaction of the radiation with the tissue to melt the distal end of the light transmitting element to cause material of light transmitting element, including calcium fluoride, to flow into the opening in the tissue to provide a dense, void-free, biologically compatible filling or coating.

* * * * *